United States Patent [19]

Albarda

[11] Patent Number: 4,477,395
[45] Date of Patent: Oct. 16, 1984

[54] APPARATUS FOR ADMIXING LIQUID ANESTHETICS AND RESPIRATORY GAS

[75] Inventor: Scato Albarda, Gross Schenkenberg, Fed. Rep. of Germany

[73] Assignee: Drägerwerk Aktiengesellschaft, Fed. Rep. of Germany

[21] Appl. No.: 368,388

[22] Filed: Apr. 14, 1982

[30] Foreign Application Priority Data

Apr. 29, 1981 [DE] Fed. Rep. of Germany ....... 3116951

[51] Int. Cl.³ .................. B01F 3/04; A61M 16/00
[52] U.S. Cl. .................... 261/131; 261/129; 261/142; 261/DIG. 65; 128/203.14; 128/203.27; 219/272
[58] Field of Search ............. 128/203.12, 203.14, 128/203.17, 203.25, 203.27; 219/272, 275, 276; 261/129, 131, DIG. 65, 142

[56] References Cited

U.S. PATENT DOCUMENTS 2,888,922 6/1959 Bellville ..................... 128/203.14
3,251,361 5/1966 Rusz ........................ 128/203.25
3,303,883 9/1975 Pecina et al. ............... 128/203.27
4,201,204 5/1980 Rinne et al. ................ 128/203.27
4,369,777 1/1983 Lwoff et al. ................ 128/203.27

Primary Examiner—Henry J. Recla
Attorney, Agent, or Firm—McGlew and Tuttle

[57] ABSTRACT

An apparatus is disclosed for admixing anesthetic with respiratory gas to be supplied to a patient, which comprises a mixing chamber having an inlet for receiving the liquid anesthesia and the respiratory gas, and an outlet for supplying the mixture. A feed line is provided in the inlet for the liquid anesthesia, with a heat exchanger for equalizing the inlet temperatures of the anesthesia and respiratory gas. Temperature sensors are provided in the inlet and the outlets with a circuit for determining the difference between the temperatures. Without heating of the chamber this difference is proportional to a ratio between the evaporated anesthetic and respiratory gas. With the chamber heated to equate the inlet and outlet temperatures, the amount of heating is proportional to the flow of anesthetic to the chamber.

10 Claims, 2 Drawing Figures

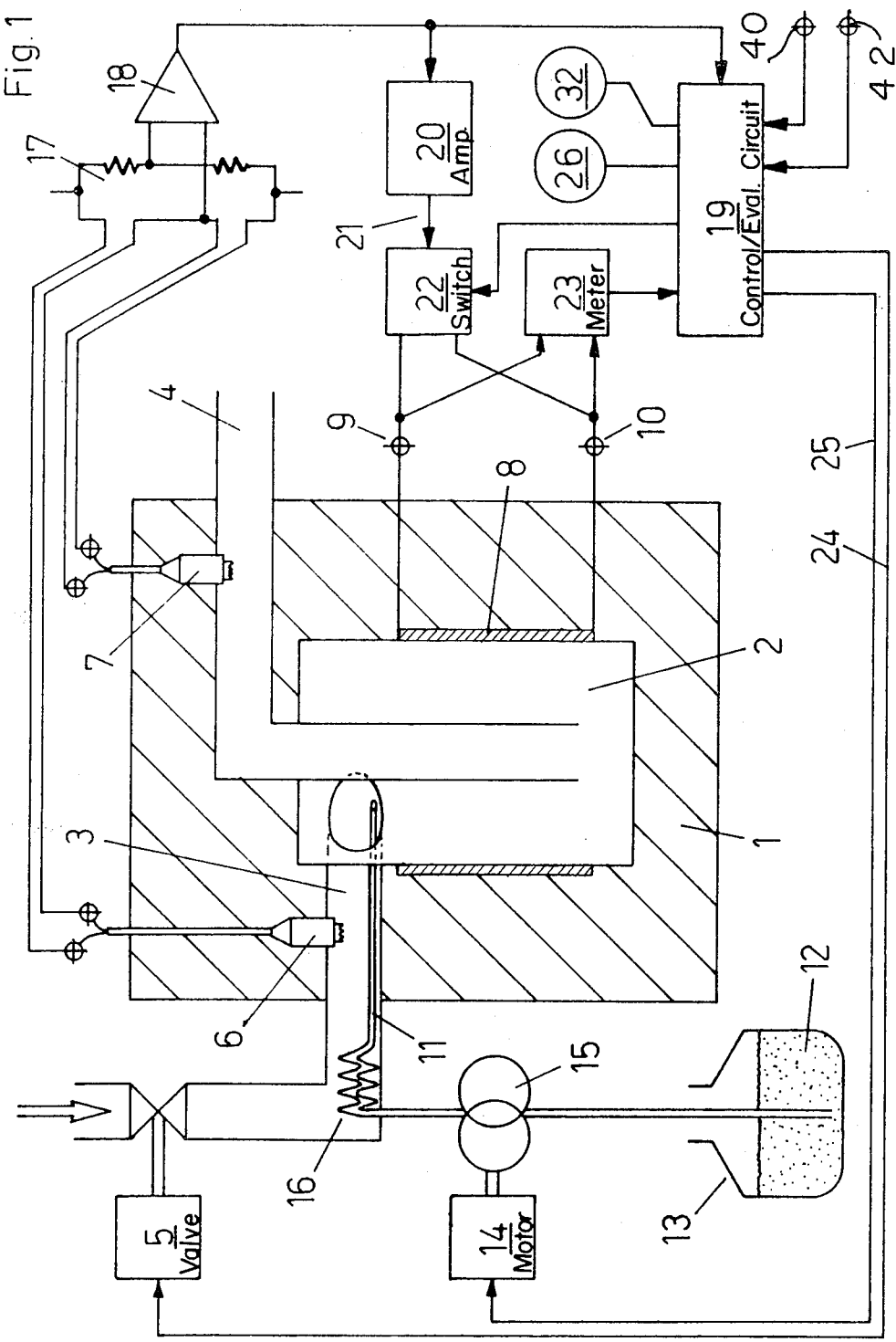

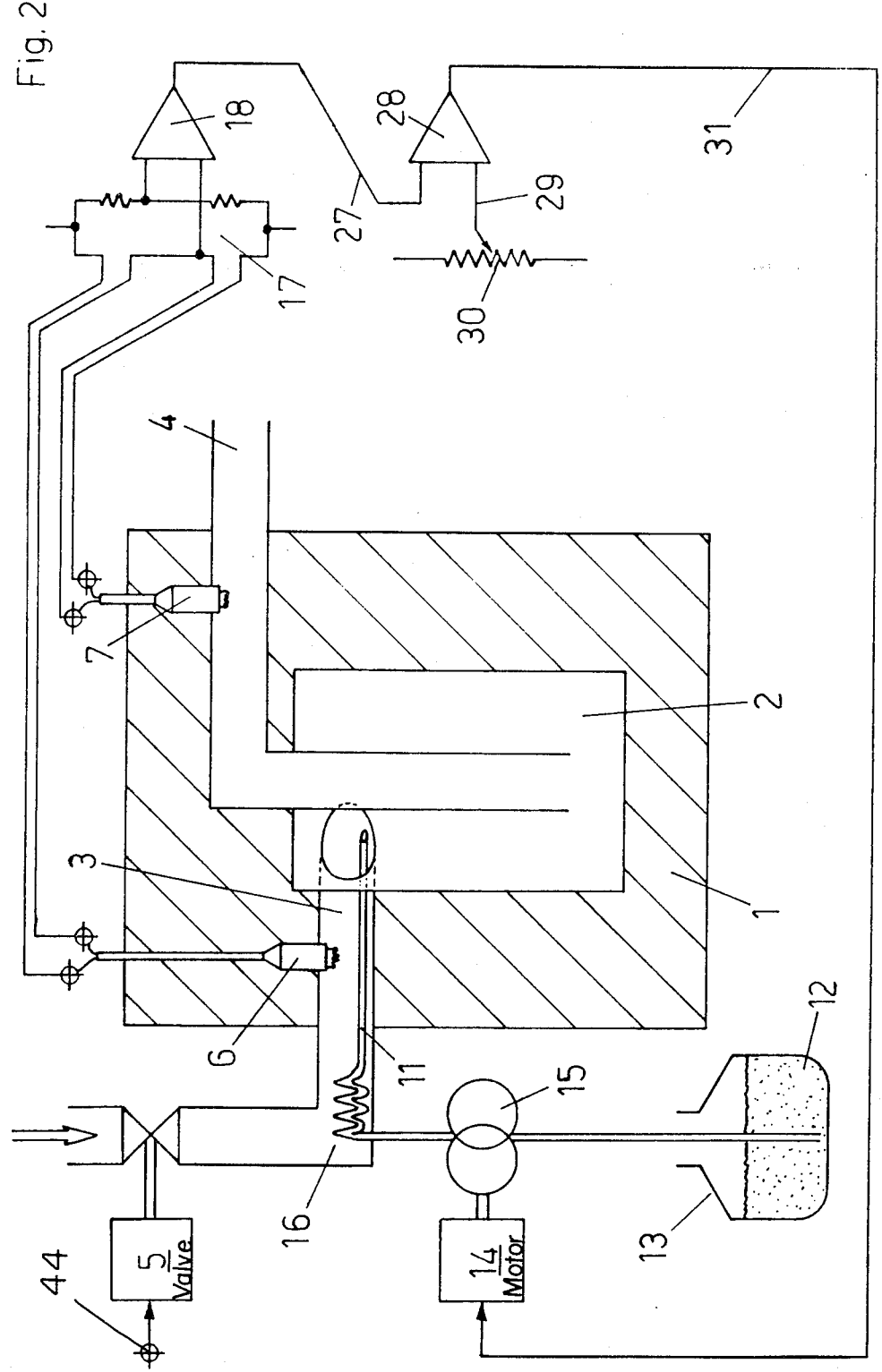

APPARATUS FOR ADMIXING LIQUID ANESTHETICS AND RESPIRATORY GAS

FIELD AND BACKGROUND OF THE INVENTION

The present invention relates in general to equipment for mixing a vaporizable liquid with a gas flow, and in particular to a new and useful apparatus and method for admixing liquid anesthetics with respiratory gas supplied to a patient.

In medical equipment, in which any failure may lead to life-threatening conditions for the patient, it goes without saying that components or their arrangements are monitored by other components that function independently or that linkages exist in the equipment, which give signals if there are differences between the actual and nominal values. With the signal, visual or auditory alarms are set off and/or automatic corrective measures, such as the switching to reserve assemblies, are initiated. The following known apparatus does not have such control capabilities.

In this known apparatus for admixing liquid anesthetics into the respiratory gas to be supplied to the patient, a gas metering device is arranged in the respiratory gas feed to the patient and one or more injection pumps for the anesthetics are connected. It further comprises one or more cylinders with plungers that are adjustable in their immersion depth, in which the anesthetic supply ends. The immersion depth is dependent on the quantity of respiratory gas flowing to the patient in a manner which is controlled via levers. The anesthetic displaced from the cylinders by the immersion of the plungers is introduced or injected into the respiratory gas stream. The lever control can be effected by a double piston moving in a cylinder, the piston being moved alternately by the respiratory gas flowing in from the patient. This known apparatus is operated by the pressure of the respiratory gas. Besides the crucial disadvantage pointed out above, of lacking control, it must be noted also that the friction forces possibly varying at the gas double pistons and in the lever system must be overcome. Owing to this, then, the gas quantity per stroke and hence the anesthetic concentration changes, so that the concentration is thus friction dependent. The dry cylinder seals used are subject to heavy wear as well. (See German Pat. No. 12 71 902).

SUMMARY OF THE INVENTION

It is the object of the present invention to provide an apparatus for admixing liquid anesthetics into respiratory gas to be supplied to a patient which, in a simple and functioning arrangement, fulfills the requirements of safe monitoring by the operating personnel and/or the automatic initiation of corrective measures.

Accordingly, an object of the invention is to provide an apparatus for admixing a vaporizable liquid with a gas comprising, a housing defining a mixing chamber, an inlet conduit connected to the housing for a flow of gas to the chamber, a liquid feed line in the inlet conduit for supplying liquid to the chamber, the feed line including a heat exchanger for equalizing the inlet temperature of the liquid with the inlet temperature of the gas in the inlet conduit, a first temperature in the inlet conduit sensing the inlet temperature, an outlet conduit connected to the housing for a flow of vaporized liquid plus gas mixture from the chamber, a second temperature sensor in the outlet conduit for sensing the outlet temperature of the mixture, liquid supply means connected to the feed line and gas supply means connected to the inlet conduit for controlling the flow of liquid and gas respectively to the chamber, nominal value set means connected to the liquid and gas supply means for controlling the supply means to supply liquid and gas at selected levels, and temperature difference measuring means connected to the first and second temperature sensors and to at least one of the liquid and gas supply means for measuring a difference between the inlet and outlet temperatures, which difference is proportional to the ratio between vaporized liquid concentration and gas concentration.

A further object of the invention is to provide such an apparatus which includes heating means connected to the housing for heating the chamber by a selected amount, the temperature difference measuring circuit means including a temperature difference measuring circuit and a control and evaluation circuit, a switch connected to the heating means and controllable by the control and evaluation circuit, the temperature difference measuring circuit connected to the switch for applying power to the heating means proportional to the difference between the inlet and outlet temperatures to reduce the difference to zero, the amount of power supplied to the heating means being a measure of the flow of anesthetic to the housing.

A still further object of the invention is to provide such an apparatus wherein the control and evaluation circuit includes indicators for indicating a deviation of the actual liquid and gas flow from the nominal values therefor.

The inventive arrangement offers the possibility of control both of the liquid, here the anesthetic, and of the gas, here the respiratory gas. In a first measuring position (a) for monitoring the anesthetic flow, it is ascertained if the actual value of the heat absorbed for the vaporization of the liquid concords with the nominal value. If not, that is, if the respective warning lamp lights up, this indicates either a pump malfunction, that is the pump did not convey the nominal volume, or that the operator did not replenish the anesthetic liquid. In the second measuring position (b) the cooling of the gas-vapor mixture is compared with a nominal value. If they are not identical, again the respective warning lamp lights up, the anesthetic concentration, i.e., the concentration of the vaporizing anesthetic in the respiratory gas, is not correct. This may be due, if the nominal value (a) is respected, either to deviations of the respiratory gas flow, e.g. through failure of the respiratory gas valve, or because the gas is the wrong specific heat, that is, the wrong gas is being supplied.

The apparatus according to the invention proves to be a simple, safe and yet informative device.

The inventive principle of measurement can in addition be used generally wherever vaporizing liquids are to be admixed to a gas stream in a defined manner. For example, the admixture of vaporizing fuels to the primary air of an Otto engine or the adjustment of a planned relative moisture in a room or in respiratory air, can be controlled.

The quantity of heat required for temperature equalization between the liquid and the gas stream is always small as compared with the quantity of heat required for evaporation. For applications where the requirements of accuracy are lower, the temperature equalization and the joint admission with heat exchanger provided for that purpose, may therefore be dispensed with in the interest of a simpler construction, without going outside the scope of the invention.

The various features of novelty which characterize the invention are point out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic block diagram of the invention which shows an apparatus for monitoring, (a) the anesthetic flow and, (b) the respiratory gas flow; and FIG. 2 is a similar view of an apparatus for maintaining the anesthetic concentration, according to the invention.

DESCRIPTION OF THE PREFERRED EMBODIMENTS

Referring to the drawings in particular, the invention embodied therein in FIGS. 1 and 2 comprise an apparatus for admixing liquid with gas, in particular liquid anesthetics with respiratory gas, to control liquid and gas supply means so that they supply nominal values of the liquid and gas flow rate to a mixing chamber.

A heat insulating housing 1 contains a measuring chamber 2 with an inlet 3 and an outlet 4. An electrically controlled respiratory gas valve 5 and an inlet temperature sensor 6 are mounted in inlet 3. A temperature sensor 7 is mounted in outlet 4. The wall of the measuring chamber 2 contains, as heating means, an electric heating element 8 with leads 9,10.

A feed line 11 for liquid anesthetic 12 ends in the inlet 3. It goes from an anesthetic vessel 13 via a proportioning pump 15 driven by a motor 14 to approximately the tangential feed of inlet 3 into the measuring chamber 2. Before the inlet temperature sensor 6, the feed line 11 includes a heat exchanger 16 in the form of coils so that the temperature of anesthetic 12, before it is vaporized can be equalized with that of respiratory gas in inlet 3.

The respiratory gas is supplied at inlet 3 and thence enters the (cylindrical) measuring chamber 2 tangentially. In the resulting cyclone type flow the liquid anesthetic 12, supplied through line 11, vaporizes and in so doing becomes mixed uniformly with the respiratory gas. Compensated by the heat exchanger 16, the respiratory gas and the liquid anesthetic 12 have, before entering the measuring chamber 2, the same temperature, which is measured by the inlet temperature sensor 6. The outlet temperature sensor 7 measures the temperature of the issuing anesthetic respiratory gas mixture. Temperature differences between the inlet and outlet 3, 4 as sensed by sensors 6, 7 are caused both by the heat of evaporation of anesthetic 12 and the flow of gas. The temperature sensors 6, 7 are resistance sensors and form part of a bridge circuit 17 whose output (difference) signal is sent via an amplifier 18, firstly to a control and evaluating circuit 19 and secondly to an amplifier 20. The output 21 of amplifier 20 is connected to the leads 9, 10 of the heating element or system 8 via a switch 22 which is controlled by the control and evaluating circuit 19. Amplifier 20 produces a current for heating element 8 which is proportional to the difference signal from amplifier 18. A wattmeter 23 is connected by its inputs with the leads 9, 10 of the heating system 8 and by its output with the control and evaluating circuit 19.

The control and evaluating circuit 19 has a set point corresponding to a nominal value for the anesthetic flow and a set point corresponding to the nominal value for the respiratory gas flow (lines 40 and 42). Its control output 24 is connected with the respiratory gas valve 5 and its control output 25 with the motor 14 of the proportioning pump 15. It further has a warning lamp 32 for the anesthetic flow and a warning lamp 26 for the respiratory gas flow. By periodic switching its operational mode, the control and evaluating circuit 19 effects several controls: Mode (a) For monitoring the anesthetic flow, switch 22 is closed by circuit 19 and thus the heating system 8 is operated in a controlled manner until there results, at the temperature sensors 6, 7 a temperature difference of "zero" and hence at the amplifier 20 the voltage difference "zero". Note that amplifier 20 supplies power to heating system 8 in an amount proportional to the difference in temperature as set by amplifier 18. In this state the supplied heating power supplied by amplifier 20, just covers the heat of evaporation of the quantity of anesthetic supplied to chamber 2, per unit time. At this time, no additional power need be supplied by amplifier 20. External factors are excluded by the heat insulation of the housing 1. This state is independent of the respiratory gas, as the quantity thereof, composition and temperature at the inlet 3 and outlet 4 are the same. The required heating power that was needed from amplifier 20 is a measure of the anesthetic flow. This heating power is measured by the wattmeter 23 and compared with the set nominal value in the control and evaluating circuit 19. Circuit 19 controls pump 14 over line 25 to maintain the proper flow of anesthetic corresponding to the set nominal value applied to circuit 19 on line 40. In case of deviation, the warning lamp 32 lights up. Mode (b) For monitoring the respiratory gas flow, switch 22 is opened by the control and evaluating circuit 19, so that the heating system 8 is turned off (disconnected from amplifier 20). The signal of amplifier 18 is now proportional to the occurring temperature difference at the temperature sensors 6, 7, which despends on the ratio between evaporated anesthetic and respiratory gas, that is, the concentration. The signal of amplifier 18 is thus a measure of the concentration of the evaporated anesthetic in the respiratory gas. The validity of this measurement is, evidently, dependent upon a complete evaporation of liquid anesthetic, which requires a sufficiently high temperature at the outflow (sensor 7). Preheating of the incoming gas flow may be required in some cases. The value of the quotient, anesthetic flow to anesthetic concentration is then a measure of the rate of flow of respiratory gas.

This quotient is formed in the control and evaluating circuit 19 and is compared with the set nominal value for the respiratory gas flow. Circuit 19 controls valve 5 for regulating the amount of respiratory gas supplied to inlet 3, over line 24 to be within the set nominal value, which is applied to circuit 19 by line 42. In case of deviation, the warning lamp 26 lights up. The alarm which is set off, can be used to readjust the setting of the nominal values. The indication of the warning lamps 26, 32 remains, so as to call attention to the fault or error. The structure of circuit 19 to achieve the invention, is within the knowledge of the art. The circuit according to FIG. 2 is a modification which assures maintenance of the anesthetic concentration at varying respiratory gas flow by automatic regulation of the anesthetic flow. Here the output signal of amplifier 18, corresponding to the anesthetic concentration (note there is no heater) is supplied to the input 27 of an amplifier 28, to whose other input 29 a nominal value is supplied via potentiometer or setting means 30 for the desired anesthetic concentration. The output of amplifier 28 controls, via a control line 31, the motor 14 of the proportioning pump 15 and thereby maintains the set anesthetic concentration. Respiratory gas flow is set at a nominal value over adjustment 44. No heater is necessary in the embodiment of FIG. 2 since a constant flow of respiratory gas is provided by valve 5 as it is controlled by the nominal value over adjustment 44. Thus the change in temperature between sensors 6 and 7 is entirely due to the heat of evaporation of the anesthetic being vaporized with respiratory gas at the input of chamber 2.

While specific embodiments of the invention have been shown and described in detail to illustrate the application of the principles of the invention, it will be understood that the invention may be embodied otherwise without departing from such principles.

What is claimed is:

1. An apparatus for admixing a vaporizable liquid with a gas comprising:
   an insulated housing defining a mixing chamber;
   an inlet conduit connected to the housing for a flow of gas to said chamber;
   a liquid feed line in the inlet conduit for supplying liquid to said chamber, said feed line including a heat exchanger in said conduit for equating an inlet temperature of the liquid with an inlet temperature of the gas in said inlet conduit before the liquid and gas reach said chamber;
   a first temperature sensor in said inlet downstream of said heat exchanger for sensing the inlet temperature;
   an outlet conduit connected to said housing for a flow of vaporized liquid plus gas mixture from said housing;
   a second temperature sensor in said outlet conduit for sensing an outlet temperature of the mixture;
   liquid supply means connected to said feed line for supplying liquid at a selected liquid flow rate;
   gas supply means connected to said inlet conduit for supplying gas at a selected gas flow rate;
   liquid flow setting means connected to said liquid supply means for controlling said selected liquid flow rate to meet a nominal value for the liquid flow;
   gas flow setting means connected to said gas supply means for controlling said selected gas flow rate to meet a nominal value for the gas flow; and
   temperature difference circuit means connected to said first and second temperature sensors and connected to said liquid flow setting means for measuring a difference between said inlet and outlet temperatures, which difference is proportional to a ratio between the concentration of evaporated liquid and respiratory gas in the mixture to obtain an actual liquid flow rate for comparison with the nominal value for the liquid flow.

2. An apparatus according to claim 1, wherein the liquid is liquid anesthetic and the gas is respiratory gas, the mixture comprising a mixture of vaporized liquid anesthetic and respiratory gas, said temperature difference circuit means including a first amplifier connected to said first and second temperature sensors having an output for carrying a signal corresponding to the difference between said inlet and outlet temperatures, a second amplifier having an inlet connected to said first amplifier outlet, said liquid flow setting means being for setting a nominal value of anesthetic flow rate and connected to a second input of said second amplifier, an output of said second amplifier connected to said liquid supply means for regulating the flow of liquid anesthetic.

3. An apparatus according to claim 1, including heating means connected to said housing for heating a mixture in said chamber, a switch connected to said heating means for applying heating power thereto, said temperature difference circuit means comprising a temperature difference circuit connected to said first and second sensors for generating a signal proportional to the difference between said inlet and outlet temperatures, said gas and liquid flow setting means comprising an evaluation circuit having an input connected to said temperature difference circuit, said evaluation circuit connected to said switch and said temperature difference circuit connected to said switch, said evaluation circuit operable to close said switch to apply heating power to said heating means which is proportional to a signal from said temperature difference circuit to equate said inlet temperature with said outlet temperature, and heat power sensing means connected to said heating means and connected to said evaluation circuit for sensing an amount of the heating power, said amount of heating power proportional to the amount of flow of liquid to said chamber.

4. An apparatus according to claim 3, wherein said liquid supply means comprises a pump and motor connected to said feed line, said gas supply means comprising a valve connected to said inlet conduit.

5. An apparatus according to claim 4 including liquid flow warning means and gas flow warning means connected to said evaluation circuit and operable upon deviation of an actual value of liquid and gas flow respectively from selected nominal values therefor.

6. An apparatus according to claim 3 wherein said chamber is cylindrical, said heating means comprising a cylindrical heating element and an interior wall of said chamber.

7. An apparatus according to claim 1 wherein said chamber is cylindrical, said inlet conduit discharging tangentially into said cylindrical chamber to facilitate admixture of the liquid and gas therein.

8. An apparatus according to claim 1 wherein said heat exchanger comprises a coil in said feed line, disposed in said inlet conduit.

9. An apparatus for admixing vaporizable liquid anesthetic with respiratory gas comprising:
   an insulated housing defining a mixing chamber;
   an inlet conduit connected to said housing for a flow of gas to said chamber;
   a liquid feed line in said inlet conduit for supplying liquid to said chamber, said feed line including a heat exchanger in said conduit for equating an inlet temperature of the liquid with an inlet temperature of the gas in said inlet conduit before the liquid and gas reach said chamber;
   a first temperature sensor in said inlet conduit downstream of said heat exchanger for sensing the inlet temperature of the gas;
   an outlet conduit connected to said housing for a flow of vaporized liquid plus gas mixture from said housing;

a second temperature sensor in said outlet conduit for sensing an outlet temperature of the mixture;

liquid supply means connected to said feed line for supplying liquid at a selected liquid flow rate;

gas supply means connected to said inlet conduit for supplying gas at a selected gas flow rate;

a temperature difference circuit connected to said first and second temperature sensors for generating a temperature difference signal proportional to a difference between the inlet and outlet temperatures;

a heater connected to said housing for heating said mixing chamber having an input for receiving heating power;

switch means connected to said heater input for activating and deactivating said heater;

an amplifier having an input connected to said temperature difference circuit for receiving said temperature difference signal and an output connected to said heater input for supplying heating power to said heater which is proportional to said temperature difference signal when said switch means activates said heater;

a power meter connected to said heater input for measuring the amount of heating power being supplied to said heater; and control/evaluation circuit means connected to said liquid supply means, said gas supply means, said switch means, said power meter and said temperature difference circuit, and adapted to receive a nominal liquid flow value and a nominal gas flow value, said control/evaluation circuit means being operable at alternate time periods to control said switch means to activate and deactivate said heater, and upon activation of said heater to measure the heating power supplied to said heater which is a measure of liquid flow to said mixing chamber, and compare said heating power with the nominal liquid flow value to control said liquid supply means for causing the selected liquid flow rate to approach the nominal liquid flow value, said control/evaluation means operable with said heater deactivated to compare said temperature difference signal which is proportional to actual gas flow rate into said mixing chamber with said heater deactivated, with the nominal gas flow value to control said gas supply means to cause the selected gas flow rate to approach the nominal gas flow value.

10. An apparatus according to claim 9, including liquid flow warning means connected to said control/evaluation circuit for generating a signal when the selected liquid flow rate cannot be made to approach the nominal liquid flow value, and gas flow warning means connected to said control/evaluation circuit for generating a warning signal when the selected gas flow rate cannot be made to meet the nominal gas flow value.

* * * * *